United States Patent [19]
Dymling et al.

[11] Patent Number: 5,056,357
[45] Date of Patent: Oct. 15, 1991

[54] ACOUSTIC METHOD FOR MEASURING PROPERTIES OF A MOBILE MEDIUM

[76] Inventors: Stephan Dymling, Rudbecksgatan 113, S-216 22 Malmö ; Tomas Hertz, Filippavägen 2 D, S-222 41 Lund; Kjell Lindström, N. Skogsvägen 3, S-236 00 Höliviken; Hans W. Persson, Thulehemsvägen 3, S-223 67 Lund, all of Sweden

[21] Appl. No.: 378,204
[22] PCT Filed: Nov. 1, 1988
[86] PCT No.: PCT/SE88/00587
§ 371 Date: Jun. 30, 1989
§ 102(e) Date: Jun. 30, 1989
[87] PCT Pub. No.: WO89/04482
PCT Pub. Date: May 18, 1989

[30] Foreign Application Priority Data
Nov. 2, 1987 [SE] Sweden .................................. 8704255

[51] Int. Cl.⁵ ............................................ G01N 11/02
[52] U.S. Cl. ............................................ 73/54; 73/53
[58] Field of Search .................. 73/32 A, 52, 53, 54, 73/590, 597

[56] References Cited
U.S. PATENT DOCUMENTS
4,112,740 9/1978 Brandestini .............................. 73/53
4,633,714 1/1987 Mazumder et al. ................... 73/596

Primary Examiner—Hezron E. Williams
Assistant Examiner—Louis M. Arana
Attorney, Agent, or Firm—Burns, Doane, Swecker & Mathis

[57] ABSTRACT

The invention relates to a method for measuring parameters and/or properties in a mobile medium, e.g. a liquid or a gas. If acoustic energy is transmitted into a mobile medium, a flow is initiated in the medium. This flow is measured providing information on the properties of the medium. If the medium contains bodies which reflect acoustic and/or optical signals, ultrasound or laser-Doppler is used for measuring the velocity of the bodies. The Doppler-shifted signal provides information on the viscosity of the medium and on the bodies in the medium.

19 Claims, 4 Drawing Sheets

ACOUSTIC METHOD FOR MEASURING PROPERTIES OF A MOBILE MEDIUM

FIELD OF THE INVENTION

The present invention relates to measuring techniques and more particularly to a method of applying acoustic energy to perform a non-destructive remote measurement and/or monitoring of properties of viscous media.

BACKGROUND OF THE INVENTION

In many areas the need for an accurate measurement and/or characterization of a series of physical parameters of liquids and gases, referred to hereinafter as mobile media, has become more and more evident. The rapid development in recent years of electronic semiconductor components has led to very powerful, fast, and inexpensive personal computers that replace in many applications where minicomputers were required. Future uses and developments of measuring, control and regulating systems are limited more through the lack of suitable measurement transmitters than of access to computer power. It does not make sense to attempt controlling an industrial process on a per mil level if the available measurement transmitter only has an accuracy of 10%.

While it is possible to measure simple parameters such as electric voltage, current, length, weight etc. with high accuracy, it is not as easy to obtain access to accurate transmitters for the measurement of more complex material properties such as lubricity, flowability, thixotropy, assessment of the quality of paper pulp etc. In the latter areas, human senses often perform better than the foremost measuring system of the day. An experienced process engineer frequently is able by the visual appearance and feel of a paper pulp to assess its suitability. Correspondingly, a physician, simply by talking to a patient, can sense whether the patient is healthy or sick, without being able directly to point to a primary reason for his feeling.

Insofar as transmitters for the type of measuring problem mentioned above are concerned, it is often not possible to specify exactly which properties of the measuring object it would be desirable to measure. More important than the absolute measuring accuracy the measurement transmitter should be consistent and, in a given measuring situation, should always provide the same measured value. Other desirable characteristics of the measurement transmitter are that it must not have a negative effect on the measuring process, and that it should be possible to carry out the measurement by means of a telemetering technique. Finally, the price of the transmitter is always important, though not wholly decisive.

For example, in the foodstuff or processing industry the need exists for continuous monitoring of the flowability or viscosity of the foodstuff product during the course of the process. The prior measurement of the viscosity is a relatively cumbersome method of analysis which involves withdrawing a sample from the process and placing it e.g. in a rotating cylinder viscosimeter. Other analyses may require the determination of the quantity of solid particles in a liquid, where the sample has to be evaporated so that the quantity of solid substance can be weighed. In many cases it is impossible for practical reasons to withdraw a sample for closer analysis. In many biotechnical processes, e.g. fermentation, the process vessel often is a closed container. To allow keeping the production at a high and even level, a continuous checking of how the process develops inside the closed vessel is desirable.

Mass production industries may experience breakdowns resulting in products of reduced quality. In such a situation, it would be desirable to rapidly and reliably separate out the faulty products from the production. It will then not be a matter of just one single point of measurement, but may involve e.g. millions of packages of non-returnable packages of milk. Naturally, it is not possible in this situation to open all packages. Rather the measuring method for the assessment of the contents should function through the unbroken package.

Against the background of the risk of many infectious diseases, such as AIDS, it may be expected that an increasing part of blood transfusions to patients with a need for blood will take place by means of so-called autologous blood transfusion. This means that before an operation patients provide their own blood which is then stored e.g. in plastic bags in cold storage, until it is needed. It will be necessary in such cases to be able to check the quality of the stored blood without opening the bags. The equipment for this purpose naturally has to be subjected to very stringent environmental requirements, e.g. sterilization.

SUMMARY OF THE INVENTION

The present invention measures certain properties of a mobile medium rapidly and without disturbing effects on the process. A signal generator drives an ultrasound transducer which transmits acoustic energy into a mobile medium. The acoustic energy generates a movement in the medium. By studying the movement using a particular measuring method information is obtained on the properties of the medium. After signal processing, this information is used to assess the physical properties of the medium.

DETAILED DESCRIPTION OF THE PREFERRED EMBODIMENT

Figure 1:
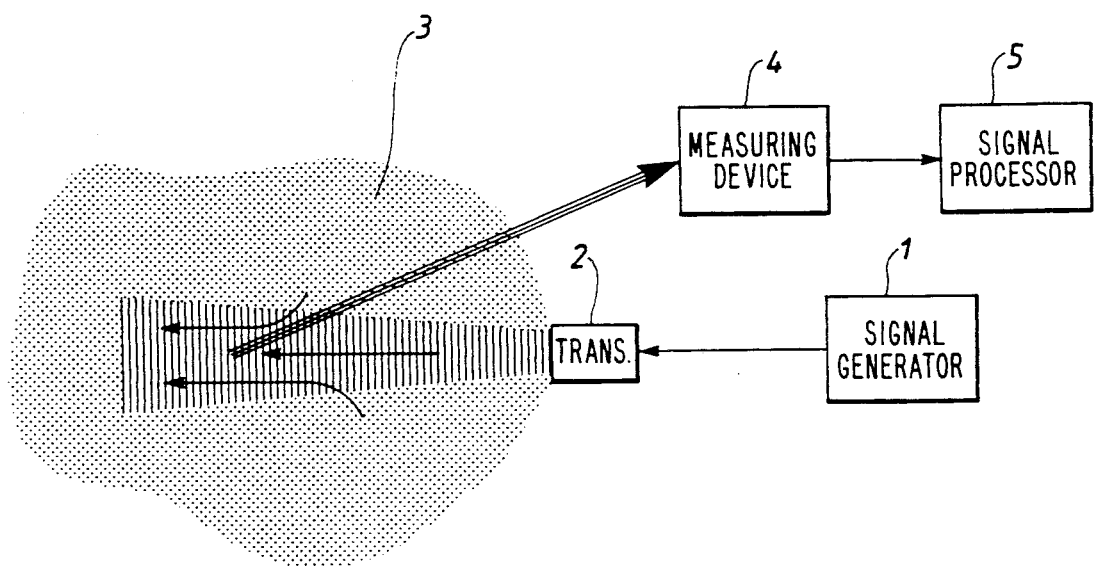
FIG. 1 is a functional block diagram for implementing one embodiment of the present invention.

A basic functional block diagram of the present invention is shown in FIG. 1. A signal generator 1 drives an ultra sound transducer 2 which transmits acoustic energy into a mobile medium 3. The acoustic energy generates a movement in the medium which is described in more detail below. A known measuring device is used to measure the movement of particles in the mobile medium in order to obtain information regarding the properties of the medium. This information is analyzed in a signal processor 5 to assess physical properties of the medium.

The acoustic signal is generated by an ultrasonics transducer of the piezoelectric type. It is known that the propagation of ultrasonic waves through a viscous medium is associated with a unidirectional movement in the medium and is called "acoustic flow". In principle, the acoustic flow is divided into two main types. The first type relates to the passage of a plan acoustic wave through an attenuating medium. The resulting acoustic flow is known as "quartz wind". The second type of acoustic flow is associated with inhomogeneities in a sound field or the joint action between a sound field and changes in impedance at boundary faces. For a more detailed description of this phenomenon reference is made to "Methods of experimental physics," Vol. 19, Ultrasonics, Editor: Peter D. Edmonds, Academic Press, 1981.

Other parameters which affect the magnitude of the movement are the viscosity of the medium, the frequency and intensity and shape of the acoustic signal transmitted, and the distance to surrounding stationary waves. If bodies are present in the medium which reflect the acoustic signal, these will be affected by a radiation pressure proportional to the intensity of the acoustic signal. The term "body" hereinafter refers to a region in the medium with an acoustic impedance different from that of the medium environment, for example particles in a liquid or liquid drops in a gas. The bodies in the medium are acted upon by a force, whose magnitude depends on the intensity of the acoustic signal causing those bodies to be put in motion relative to the surrounding medium. The amount of this movement depends on the magnitude of the force, the physical properties of the surrounding medium, the size of the bodies, etc. The movement of the bodies in relation to the ultrasonics transducer depends on the movement of the surrounding medium as well as on the bodies' own movement in relation to the surrounding medium.

Many different methods may be used for measuring the movement of bodies in the medium. Examples of practical measurement situations are set forth in various preferred embodiments with a description of how properties of the actual medium can be measured according to the principle of the present invention.

A medium is enclosed in a sealed container and the task of the measurement consists in determining the movement of the medium without having to open the container. Such a task may be considered to occur in connection with the aforementioned problem which may be that of checking whether milk packaged sterile is fresh, or whether blood in the blood bags has commenced to deteriorate. In both these cases, bodies are present in the medium, fat emulsion and blood corpuscles, respectively, so that a Doppler technique may be applied for the detection of the relative movement of the bodies. A preferred embodiment of the invention is illustrated in accordance with FIG. 2, which uses a continuous ultrasound Doppler technique. A signal generator (6) with a suitably chosen output and frequency drives an ultrasound transducer (7) to generate acoustic energy which is transmitted into the medium (8) through the package wall. This is an acceptable technique, since most packing material does not constitute any major obstacle for an acoustic wave. A part of the acoustic energy transmitted into the medium is reflected by the bodies in the medium and is frequency shifted in accordance with the Doppler effect. In the case of non-returnable packages manufactured from paper or cardboard, the acoustic energy is introduced through a wall portion where the paper or cardboard material has been removed and replaced by a cover foil of homogeneous material. Likewise, the reflected acoustic waves are picked up through a wall portion where the paper or cardboard material has been removed and replaced by a cover foil of homogeneous material.

The magnitude of the frequency shift, f, given by $$f = (k \cdot v \cdot f)/c$$

where
 f = Doppler shift
 k = constant, depending on the actual measuring situation
 v = velocity of the bodies
 f = frequency of the acoustic signal transmitted
 c = velocity of sound in the medium It follows from the above that the magnitude of the frequency shift is directly proportional to the velocity of the bodies. The reflected signal is detected using a second ultrasound transducer (9). The frequency-shifted part of the signal received, the Doppler shift, is separated by multiplying the signal received by the transducer (9) by the signal from the signal generator (6) in a mixer (10). The magnitude of the Doppler shift can be measured thereafter in a frequency analyzer (11).

In this case it is possible to use the same acoustic energy both for generating movement in the medium and for measuring the resulting flow. Since the bodies have been put in motion by the acoustic signal and their velocity is a function of factors named above, inter alia the intensity of the signal and the viscosity of the medium, the velocities of the bodies and therefore the frequency content of the Doppler shift will constitute an indicator of the viscous properties of the medium, provided other parameters, such as the signal intensity, are known. It is interesting to note that the method according to the present invention for measuring properties of the medium is not limited by the signal-to-noise ratio of the ultrasound Doppler method.

The intensity of the Doppler-shifted signal is a direct measure of how great a part of the signal introduced has been reflected by the mobile bodies in the medium. The reflected intensity depends among other things on the number of the bodies and their acoustic cross-sectional plane. Because the acoustic cross-sectional plane of the bodies may be determined from a reference solution, the intensity of the Doppler signal constitutes a measure of the quantity of mobile bodies in the medium. Doppler-shifts in the mobile medium may be compared with corresponding shifts in a reference medium which is subjected to the same acoustic energy. In order to increase the reproducibility of the measurements, the Doppler-shifted signal may be standarized by dividing it by the non-frequency-shifted, reflected acoustic signal.

The reflecting bodies are accelerated to different velocities in the medium as a function of the appearance of the flow profile in the "sensitive volume" or because the different bodies having varying size or acoustic impedance. As a result, the Doppler effect will contain a number of different frequency components with diverse amplitudes, where the respective amplitude, inter alia, depends on the product of quantity times acoustic cross-sectional plane. A frequency analyzer (11) determines which frequencies enter into the Doppler signal as well as their relative intensities. Correspondingly, it is advantageous in certain measuring situations to use other types of Doppler measuring techniques, e.g. direction-sensing Doppler or pulsed Doppler technique, which both bring about an improved spatial resolution of the measurements and detection of other flow directions, turbulence etc. The pulsed Doppler, moreover, can perform measurements at a variable distance from the ultrasound transducer. By the combination of several such measurements, independent parameters of the mobile medium can be determined.

The frequency content of the Doppler signal provides information on the velocities of the bodies in the medium in relation to transmitter and receiver, which is a well-known property of the ultrasound Doppler equipment used at present, inter alia, in infirmaries for non-invasive blood flow measurements. The analogy is not quite perfect, however, since in the normal medical usage of ultrasound Doppler, blood flow velocities in the order of magnitude of 5–100 cm/s are measured, which are appreciably higher than the velocities which the bodies in the aforementioned measuring situation can be expected to attain. As a matter of fact, commercially available ultrasound Doppler apparatuses cannot be used for the type of measurements used in the present invention, since these apparatuses contain high-pass filters which for various reasons filter out all low-frequency Doppler signals corresponding to velocities below approx. 5 cm/s.

In a dissertation from the Lunds Tekniska och Naturvetenskapliga Högskola (Technical and Scientific University of Lund), "Measurement of blood perfusion in tissue using Doppler ultrasound", LUTEDX/(TEEM-1027)/1-4(1985), Stephan Dymling recently has shown that it is possible to design highly stable Doppler measuring equipment with performances which also manage to measure the extremely small Doppler shifts which a measuring equipment according to the present invention is expected to produce.

Figure 2:
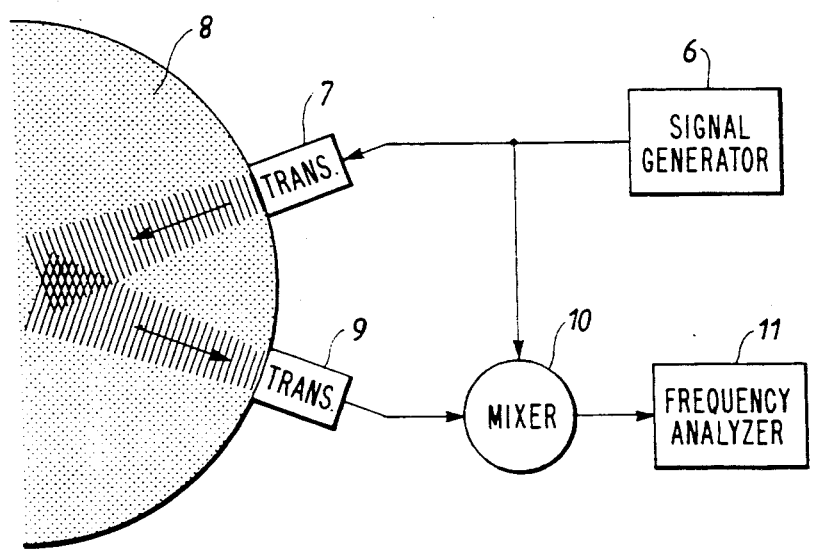
FIG. 2 is a functional block diagram for implementing the preferred embodiment of the present invention.
Figure 3A:
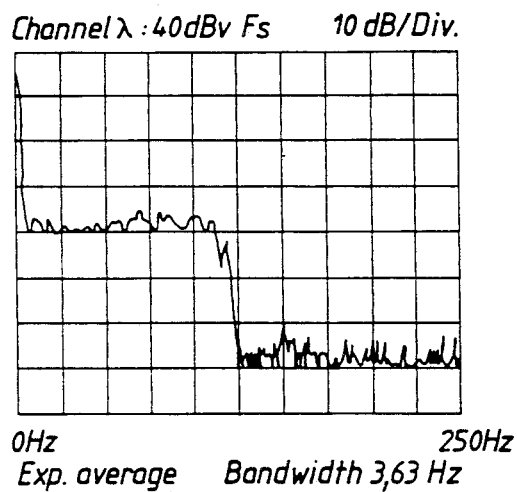
FIGS. 3A-3D are frequency spectrum graphs of mobile medium resulting from the acoustic measuring method according to the present invention.
Figure 3B:
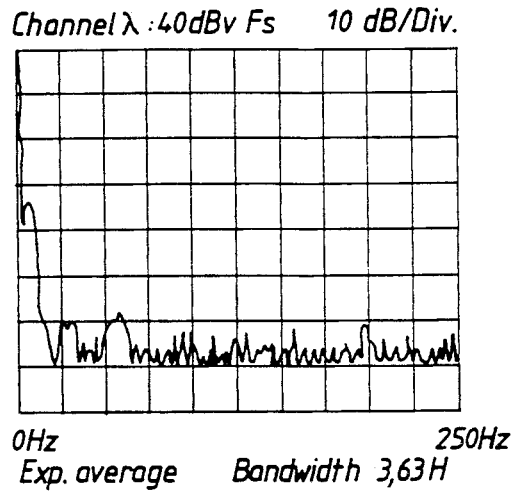
Figure 3C:
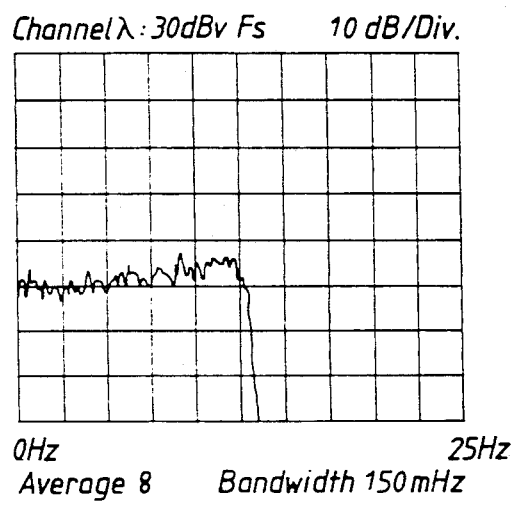
Figure 3D:
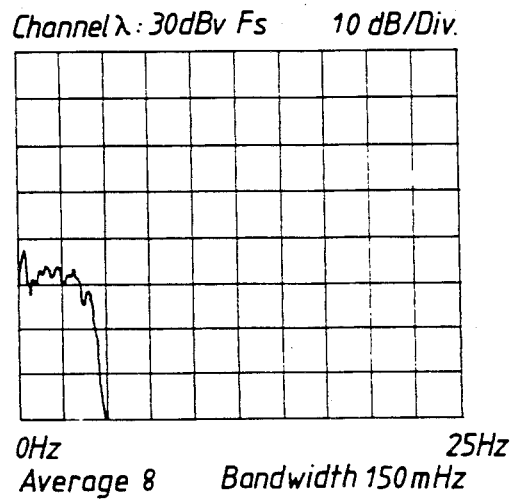

For further clarification of the method of measurement according to the preferred embodiment illustrated in FIG. 2, a practical application of the present invention is used to measure viscosity changes in milk. For the signal generator (6) a highly stable oscillator is required, such as a crystal oscillator or a crystal-controlled synthesis generator with a frequency stability of better than $10^{-7}$. The signal used is selected as a function of the actual measuring medium: For milk a frequency of 10 MHz and an amplitude of 1–10 V are suitable starting values. This signal drives an ultrasound transducer which may consist of a piezoelectric material such as e.g. Ferroperm type PZ.

The acoustic energy transmitted in fresh milk will have an acoustic intensity of the order of magnitude of 100 mV/cm$^2$, which results in an acoustic flow of approx. 1 cm/s. The reflected ultrasound signal, which is detected by the ultrasound transducer (9), is therefore Doppler-shifted. Using the mixer (10), the Doppler shift, which in this case should be of the order of magnitude 100 Hz, is detected. The Doppler signal detected is analyzed using a Hewlett Packard Spectrumanalyzer model 3582A frequency analyzer (11) and the measuring result is substantiated through digital data storage or through printout on a plotter.

With this equipment, practical measurements can be carried out and some measuring results are represented in FIG. 3. FIG. 3A shows a frequency spectrum of the Doppler shift signal from a measurement of fresh milk whereas FIG. 3B shows how the spectra have been changed after the milk had been stored for 2 days at room temperature. It can be seen clearly that in the deteriorated milk the particles move at lower velocity. FIG. 3C shows a frequency spectrum of the Doppler signal on measuring warm (35° C.) glycerol with addition of reflecting bodies, and FIG. 3D shows corresponding spectra after the temperature has been lowered to 20° C. The reduced Doppler shift agrees well with previously known facts suggesting that the viscosity of glycerol is a function of the temperature.

Figure 4:
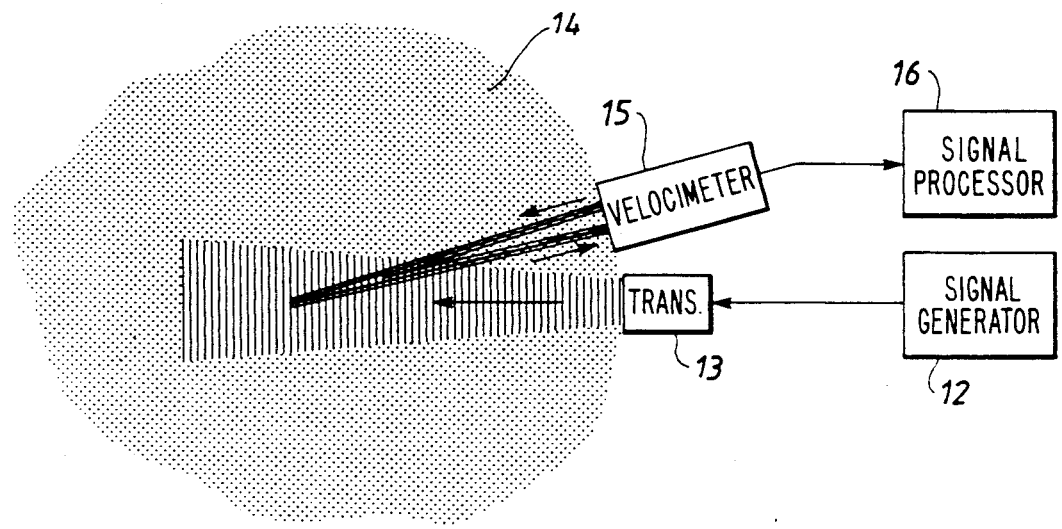
FIG. 4 is a functional block diagram for implementing another embodiment of the present invention.

In another embodiment, instead of using the acoustic Doppler technique, it is also feasible, if the bodies have an optical impedance which differs from that of the surrounding medium, to use an optical Doppler technique for measuring the resulting acoustic flow. The measuring technique using optical Doppler is described in accordance with FIG. 4. A signal generator (12) with suitably chosen output and frequency drives an ultrasound transducer (13) to generate acoustic energy in the medium (14) (corresponding to 6,7 and 8 in FIG. 2). The measuring method now uses optical laser Doppler (15), whereafter the measuring signal obtained is processed in signal processor (16). The advantage of the laser Doppler is in the possibility of obtaining very good spatial resolution, that is to say permitting measurement of the movement at a single point. The disadvantage is that this measurement method functions only in more or less transparent media.

Figure 5:
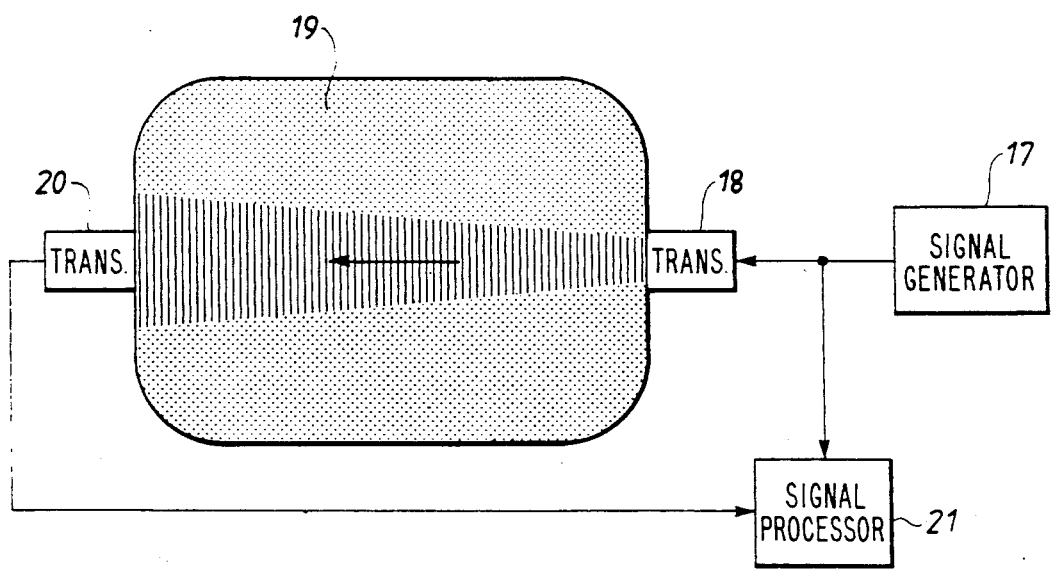
FIG. 5 is a functional block diagram for implementing another embodiment of the present invention.

In certain media it is not possible to use Doppler technique as a measuring method for the detection of the acoustic flow, e.g. when the medium does not contain any reflecting bodies. However in such cases an acoustic flow may be developed e.g. through the aforementioned "quartz wind". FIG. 5 shows a preferred embodiment for measuring acoustic flow in this situation. The acoustic energy is generated in the medium (19) using a signal generator (17) and an ultrasound transducer (18). Instead of measuring the reflected energy, the transmitted sound signal is detected using a second ultrasound transducer (20). The actual measurement of the acoustic flow, may be accomplished in a number of different ways: a) through phase comparison by the signal processor (21) of the transmitted and the detected acoustic signals, b) through the generated signal containing a repetitive transient disturbance whose transmission time to the transducer (20) is measured by the signal processor (21), or c) through generation by the signal generator (17) of a randomized signal whose transmission time up to the transducer (20) is detected using a correlation technique in the signal processor (21).

Figure 6:
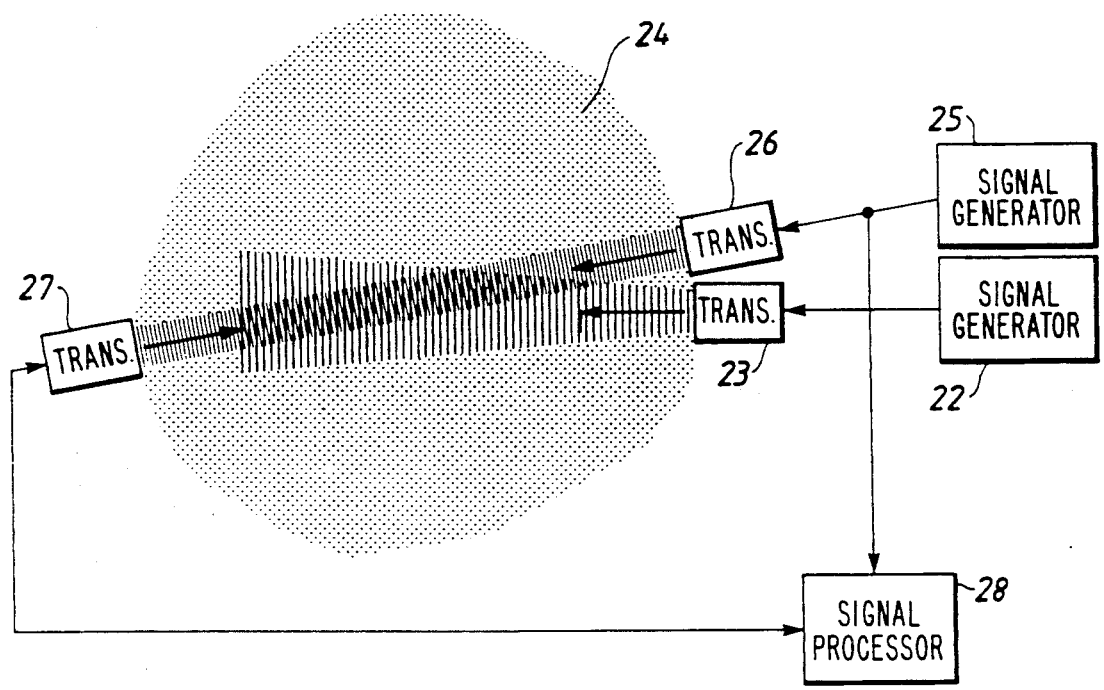
FIG. 6 is a functional block diagram for implementing another embodiment of the present invention.

Another preferred embodiment for carrying out the measurement of acoustic flow is shown in FIG. 6. The acoustic flow in the medium (24) is generated from the signal generator (22) via the ultrasound transducer (23). The measurement is determined from the transmission time using two other ultrasound transmitters (26) and (27). The measuring signal may be ultrasonic energy of a different ultrasonic frequency or it may consist of any form of pulse sequence where phase or cycle time are measured in (28). Finally the measurement naturally also can be carried out by means of a "sing-around"-technique.

Regardless of the measuring method, it is possible before the start of the actual measurement, that is to say before the acoustic energy is supplied to the medium, to use the measuring method in order to investigate the presence of any disturbing movements in the medium.

This may be applied as an autotest to assess how far it is possible to use the measuring method in the particular measuring technique and regarding the expected signal-to-noise level for the coming measurement. With a suitable signal processing technique, measurements of physical properties may take place also on media in motion, e.g. in conveyor pipe lines. By variation of the intensity of the acoustic signal transmitted, other properties of the medium can be investigated, especially non-linear properties such as thixotropy, etc. By watching the acceleration of the acoustic flow when the acoustic energy is introduced, further information concerning the medium concerned can be obtained.

Beside the aforementioned examples from infirmary, foodstuffs and processing industry, the present invention can be applied in many other fields, for monitoring the condition of cooking oils in hamburger restaurants, cutting oils in machine tools and lubricating oils in cars.

Many modifications are possible within the scope of the invention. While this invention has been illustrated and described in accordance with the number of preferred embodiments, it is recognized that variations and changes may be made therein without departing from the invention as set forth in the claims.

We claim:

1. A method for determining changes in viscosity and other properties of a medium including a liquid and substances suspended in or blended into the liquid, said substances having an acoustic impedance differing from said liquid, comprising:
   (a) transmitting acoustic waves into the medium causing a flow movement in said medium;
   (b) detecting acoustic waves that have passed through the medium;
   (c) calculating a difference in frequency between said transmitted acoustic waves and said detected acoustic waves; and
   (d) determining a relative measure of the velocity between said liquid and said substances based on said difference.

2. A method according to claim 1, wherein said transmitted and detected acoustic waves are ultrasound waves having a frequency between 20 kHz and 100 MHz.

3. A method according to claim 1, wherein said detecting step (b) includes detecting acoustic waves that have been reflected in the medium, and said calculating step (c) includes comparing the frequency spectrum of said reflected acoustic waves with the frequency of said transmitted acoustic waves.

4. A method according to claim 1, wherein said calculating step (c) includes calculating a phase shift between said transmitted waves and said detected waves, and said determining step (d) includes determining a relative velocity between said liquid and said substances based on said phase shift.

5. A method according to claim 1, wherein said calculating step (c) and determining step (d) utilize Doppler techniques.

6. A method according to claim 5, wherein said calculating step (c) includes standardizing Doppler-shifted wave components.

7. The method according to claim 1, wherein said flow movement of said medium is detected by measuring the time for said transmitted acoustic waves to be detected in said detecting step (b).

8. A method according to claim 1, further comprising:
   (e) transmitting acoustic waves into a reference medium causing a flow movement in said reference medium;
   (f) detecting acoustic waves that have passed through said reference medium;
   (g) calculating a reference difference in frequency between said acoustic waves transmitted in said reference medium and said acoustic waves detected in said reference medium;
   (h) determining a relative measure of the velocity of the liquid and substances in said reference medium based on said reference difference; and
   (i) comparing the velocity determined in step (h) with the velocity determined in step (d).

9. The method according to claim 1, further comprising:
   measuring the quantity of mobile reflecting bodies in said medium as a function of the intensity of said frequency difference between said transmitted and detected acoustic waves.

10. A method according to claim 1, wherein the intensity of said transmitted acoustic waves is varied during said detecting step.

11. A method according to claim 1, wherein said other properties include the occurrence of gas bubbles and solid particles in said medium.

12. A method according to claim 1, wherein said medium is enclosed in a package.

13. A method according to claim 12, wherein said package is composed of paper.

14. A method according to claim 12, wherein said package is composed of cardboard.

15. A method according to claim 12, wherein said acoustic waves are transmitted and detected through a portion of said package composed of a cover foil of homogenous material.

16. The method according to claim 1, further comprising:
   comparing said relative measure of the velocity with a predetermined reference to detect a condition of said medium.

17. The method according to claim 16, wherein said medium is a foodstuff and said condition relates to spoilage of said foodstuff.

18. A method for determining changes in viscosity of a liquid medium having at least one of a gas phase and a solid phase enclosed in a package, comprising:
   introducing acoustic energy into said liquid medium through a portion of said package composed of a homogeneous material, causing a flow movement in said liquid medium;
   sensing reflected acoustic energy through a portion of said package composed of a homogeneous material; and
   determining changes in viscosity and the occurrence of at least one of said gas phase and said solid phase in said liquid medium based on a difference between said introduced acoustic energy and reflected acoustic energy.

19. A method according to claim 18, wherein said package is composed of paper or cardboard and said portion of said package is composed of a cover foil of homogeneous material.

* * * * *